United States Patent
Govari et al.

(10) Patent No.: US 10,918,306 B2
(45) Date of Patent: Feb. 16, 2021

(54) CATHETER SPLINES WITH EMBEDDED CIRCUIT ELEMENTS

(71) Applicant: Biosense Webster (Israel) Ltd., Yokneam (IL)

(72) Inventors: Assaf Govari, Haifa (IL); Andres Claudio Altmann, Haifa (IL); Christopher Thomas Beeckler, Brea, CA (US); Joseph Thomas Keyes, Glendora, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 747 days.

(21) Appl. No.: 15/376,807

(22) Filed: Dec. 13, 2016

(65) Prior Publication Data

US 2018/0160936 A1 Jun. 14, 2018

(51) Int. Cl.
*A61B 5/06* (2006.01)
*A61B 5/00* (2006.01)
(Continued)

(52) U.S. Cl.
CPC ............ *A61B 5/062* (2013.01); *A61B 5/0422* (2013.01); *A61B 5/6858* (2013.01);
(Continued)

(58) Field of Classification Search
CPC .... A61B 2018/1407; A61B 2018/1435; A61B 2018/1437; A61B 5/062; A61B 8/0841;
(Continued)

(56) References Cited

U.S. PATENT DOCUMENTS 5,391,199 A 2/1995 Ben-Haim
5,800,494 A * 9/1998 Campbell .............. A61B 18/18
606/33

(Continued)

FOREIGN PATENT DOCUMENTS

WO WO 96/005768 A1 2/1996
WO WO 2014/036439 A2 3/2014

OTHER PUBLICATIONS

Peters, Christian, and Yiannos Manoli. Inductance calculation of planar multi-layer and multi-wire coils: An analytical approach [online]. Sensors and Actuators A, 2008 [available online Nov. 17, 2007, retrieved on Jan. 21, 2020], vol. 145-146, pp. 394-404. Retrieved from the Internet: <URL/DOI: see Office action>.*

(Continued)

*Primary Examiner* — Carolyn A Pehlke
*Assistant Examiner* — Victoria Fang
(74) *Attorney, Agent, or Firm* — Frost Brown Todd LLC

(57) ABSTRACT

Medical apparatus includes one or more magnetic field generators, which are configured to generate magnetic fields within a body of a patient. An invasive probe includes an insertion tube having a distal end, which is configured for insertion into the body, and a plurality of flexible splines configured to be deployed from the distal end of the insertion tube. Each spline includes a flexible, multilayer circuit board and a conductive trace that is formed in at least one layer of the circuit board and is configured to define one or more coils, which are disposed along a length of the spline and output electrical signals in response to the magnetic fields. A processor is coupled to receive and process the electrical signals output by the coils in order to derive respective positions of the flexible splines in the body.

20 Claims, 4 Drawing Sheets

(51) Int. Cl.
*A61B 5/042* (2006.01)
*A61B 17/00* (2006.01)
*A61B 34/20* (2016.01)
*A61B 18/00* (2006.01)
*A61B 18/14* (2006.01)
*A61B 8/08* (2006.01)
*H05K 1/02* (2006.01)
*H05K 1/11* (2006.01)
*H05K 1/16* (2006.01)
*H05K 3/00* (2006.01)
*H05K 3/46* (2006.01)

(52) U.S. Cl.
CPC .......... *A61B 5/6859* (2013.01); *A61B 5/6886* (2013.01); *A61B 8/0841* (2013.01); *A61B 18/1492* (2013.01); *H05K 1/028* (2013.01); *H05K 1/11* (2013.01); *H05K 1/165* (2013.01); *H05K 3/0044* (2013.01); *H05K 3/4644* (2013.01); *A61B 2017/0011* (2013.01); *A61B 2018/00077* (2013.01); *A61B 2018/00267* (2013.01); *A61B 2018/00351* (2013.01); *A61B 2018/00577* (2013.01); *A61B 2018/00642* (2013.01); *A61B 2018/00839* (2013.01); *A61B 2018/00875* (2013.01); *A61B 2018/00988* (2013.01); *A61B 2034/2051* (2016.02); *A61B 2562/0204* (2013.01); *A61B 2562/0209* (2013.01); *A61B 2562/0223* (2013.01); *A61B 2562/125* (2013.01); *H05K 2201/10151* (2013.01)

(58) Field of Classification Search
CPC . A61B 18/1492; A61B 5/0422; A61B 5/6886; A61B 5/6859; A61B 5/6858; A61B 2090/061; A61B 2017/0011; A61B 2034/2051; A61B 2562/0223; A61B 2562/0204; A61B 2562/0209; A61B 2562/125; A61B 2018/00988; A61B 2018/00267; A61B 2018/00577; A61B 2018/00642; A61B 2018/00839; A61B 2018/00875; A61B 2018/00077; A61B 2018/00351; H05K 1/11; H05K 1/165; H05K 1/028; H05K 3/0044; H05K 3/4644; H05K 2201/10151

USPC ...................................................... 600/424
See application file for complete search history.

(56) References Cited

U.S. PATENT DOCUMENTS

| | | |
|---|---|---|
| 5,928,228 A | 7/1999 | Kordis et al. |
| 6,201,387 B1* | 3/2001 | Govari ................ G01D 5/2086 324/207.17 |
| 6,239,724 B1 | 5/2001 | Doron et al. |
| 6,332,089 B1 | 12/2001 | Acker et al. |
| 6,484,118 B1 | 11/2002 | Govari |
| 6,529,756 B1 | 3/2003 | Phan et al. |
| 6,618,612 B1 | 9/2003 | Acker et al. |
| 6,690,963 B2 | 2/2004 | Ben-Haim et al. |
| 6,748,255 B2 | 6/2004 | Fuimaono et al. |
| 2002/0065455 A1 | 5/2002 | Ben-Haim et al. |
| 2003/0078509 A1 | 4/2003 | Panescu |
| 2003/0120150 A1 | 6/2003 | Govari |
| 2003/0176816 A1* | 9/2003 | Maguire ................ A61B 18/00 601/2 |
| 2003/0233099 A1* | 12/2003 | Danaek .............. A61B 18/1477 606/96 |
| 2004/0068178 A1 | 4/2004 | Govari |
| 2006/0000969 A1 | 1/2006 | Sano |
| 2012/0143298 A1* | 6/2012 | Just ...................... A61B 5/0422 607/122 |
| 2013/0066194 A1* | 3/2013 | Seter ...................... A61B 5/062 600/424 |
| 2014/0276004 A1* | 9/2014 | Strupeck ................ A61B 5/061 600/424 |
| 2014/0350553 A1* | 11/2014 | Okuyama .......... A61B 18/1492 606/41 |
| 2015/0196354 A1 | 7/2015 | Haverkost et al. |
| 2015/0250424 A1* | 9/2015 | Govari ................ A61B 5/6858 600/373 |
| 2015/0366508 A1* | 12/2015 | Chou ....................... A61B 8/12 600/374 |
| 2016/0324474 A1* | 11/2016 | Sterrett ................ A61B 5/6852 |
| 2018/0317313 A1* | 11/2018 | Kegeler .............. H01F 27/2804 |
| 2019/0223758 A1* | 7/2019 | Just ...................... A61B 5/6852 |

OTHER PUBLICATIONS

Extended European Search Report dated May 22, 2018 for Application No. 17206730.8, 9 pages.

* cited by examiner

CATHETER SPLINES WITH EMBEDDED CIRCUIT ELEMENTS

FIELD OF THE INVENTION

The present invention relates generally to invasive medical devices, and particularly to catheters having multiple distal splines.

BACKGROUND

Some types of catheters have multiple elongate flexible segments joined together to the distal end of the catheter. These segments, which are commonly referred to as "splines," may have the form of separate arms, for example, which are joined at their proximal extremities to the catheter and open out in different directions, as in the PentaRay® catheter produced by Biosense Webster, Inc. (Diamond Bar, Calif.). Alternatively, the splines may be configured as staves of a basket, which are joined together at both their proximal and distal extremities. In cardiac electrophysiology applications, multiple sensing electrodes are attached to the splines, and are used to simultaneously measure electrical signals at multiple locations in the heart.

For example, U.S. Pat. No. 6,748,255, whose disclosure is incorporated herein by reference, describes a basket catheter for mapping the heart. The catheter comprises an elongated catheter body and at least one lumen therethrough. A basket-shaped electrode assembly is mounted at the distal end of the catheter body. The basket assembly comprises a plurality of splines connected at their proximal and distal ends. Each spline comprises at least one electrode. The basket assembly has an expanded arrangement wherein the splines bow radially outwardly and a collapsed arrangement wherein the splines are arranged generally along the axis of the catheter body.

The catheter further comprises a distal location sensor mounted at or near the distal end of the basket-shaped electrode assembly and a proximal location sensor mounted at or near the proximal end of the basket-shaped electrode assembly. In use, the coordinates of the distal location sensor relative to those of the proximal sensor can be determined and taken together with known information pertaining to the curvature of the splines of the basket-shaped mapping assembly to find the positions of the at least one electrode of each spline.

As another example, U.S. Patent Application Publication 2015/0366508, issued as U.S. Pat. No. 10,201,311 on Feb. 12, 2019, describes a flex-PCB catheter device that is configured to be inserted into a body lumen. The flex-PCB catheter comprises an elongate shaft, an expandable assembly, a flexible printed circuit board (flex-PCB) substrate, a plurality of electronic components and a plurality of communication paths. The expandable assembly is configured to transition from a radially compact state to a radially expanded state. The plurality of electronic elements are coupled to the flex-PCB substrate and are configured to receive and/or transmit an electric signal. The plurality of communication paths are positioned on and/or within the flex-PCB substrate and selectively couple the plurality of electronic elements to a plurality of electrical contacts configured to electrically connect to an electronic module configured to process the electrical signal. The flex-PCB substrate can have multiple layers, including one or more metallic layers. Acoustic matching elements and conductive traces can be included in the flex-PCB substrate.

SUMMARY

Embodiments of the present invention that are described hereinbelow provide improved multi-spline probes, as well as methods associated with such probes.

There is therefore provided, in accordance with an embodiment of the invention, medical apparatus, including one or more magnetic field generators, which are configured to generate magnetic fields within a body of a patient. An invasive probe includes an insertion tube having a distal end, which is configured for insertion into the body, and a plurality of flexible splines configured to be deployed from the distal end of the insertion tube. Each spline includes a flexible, multilayer circuit board and a conductive trace that is formed in at least one layer of the circuit board and is configured to define one or more coils, which are disposed along a length of the spline and output electrical signals in response to the magnetic fields. A processor is coupled to receive and process the electrical signals output by the coils in order to derive respective positions of the flexible splines in the body.

In some embodiments, the flexible splines have respective distal and proximal extremities and are connected together at both the distal and proximal extremities to define a basket assembly, which has a collapsed configuration, in which the splines are held parallel to the insertion tube during insertion into the body, and an expanded configuration, in which the splines bow radially outward within a cavity in the body. In one embodiment, the flexible, multilayer circuit board has a resilience sufficient to cause the splines to bow radially outward within the cavity.

Typically, the multilayer circuit board includes further conductive traces, which are connected to the one or more coils and run along the length of the splines so as to couple the electrical signals to the processor.

Additionally or alternatively, the multilayer circuit board includes electrodes, which are disposed on an outer surface of each spline so as contact tissue at respective locations within the body. The processor may be configured to map electrical activity in the body responsively to the electrical activity sensed by the electrodes and the positions of the flexible splines that are derived from the signals output by the coils.

Further additionally or alternatively, the invasive probe includes acoustic transducers that are fixed to the multilayer circuit board on one or more of the flexible splines, wherein the multilayer circuit board includes further conductive traces, which are connected to the acoustic transducers and run along the length of the splines so as to couple the acoustic transducers to the processor.

In a disclosed embodiment, the one or more coils include multiple coils disposed along the length of each of the splines, and the processor is configured to derive both locations and orientations of the splines from the electrical signals output by the coils.

There is also provided, in accordance with an embodiment of the invention, a method for medical diagnosis or treatment. The method includes generating magnetic fields within a body of a patient and inserting a distal end of an insertion tube into the body. A plurality of flexible splines are deployed from the distal end of the insertion tube into the body. Each spline includes a flexible, multilayer circuit board and a conductive trace that is formed in at least one layer of the circuit board and is configured to define one or more coils, which are disposed along a length of the spline and output electrical signals in response to the magnetic fields. The electrical signals output by the coils are processed in order to derive respective positions of the flexible splines in the body.

There is additionally provided, in accordance with an embodiment of the invention, a method for producing an invasive probe, which includes providing an insertion tube having a distal end, which is configured for insertion into the body. Multiple, successive layers of metal traces and dielectric material are deposited on a flexible polymer substrate to produce a flexible printed circuit board, including a conductive trace that is formed in at least one of the layers and is configured to define multiple coils. The flexible printed circuit board is sliced into a plurality of ribbons, which are deployed as flexible splines extending from the distal end of the insertion tube.

The present invention will be more fully understood from the following detailed description of the embodiments thereof, taken together with the drawings in which:

DETAILED DESCRIPTION OF EMBODIMENTS

Figure 1:
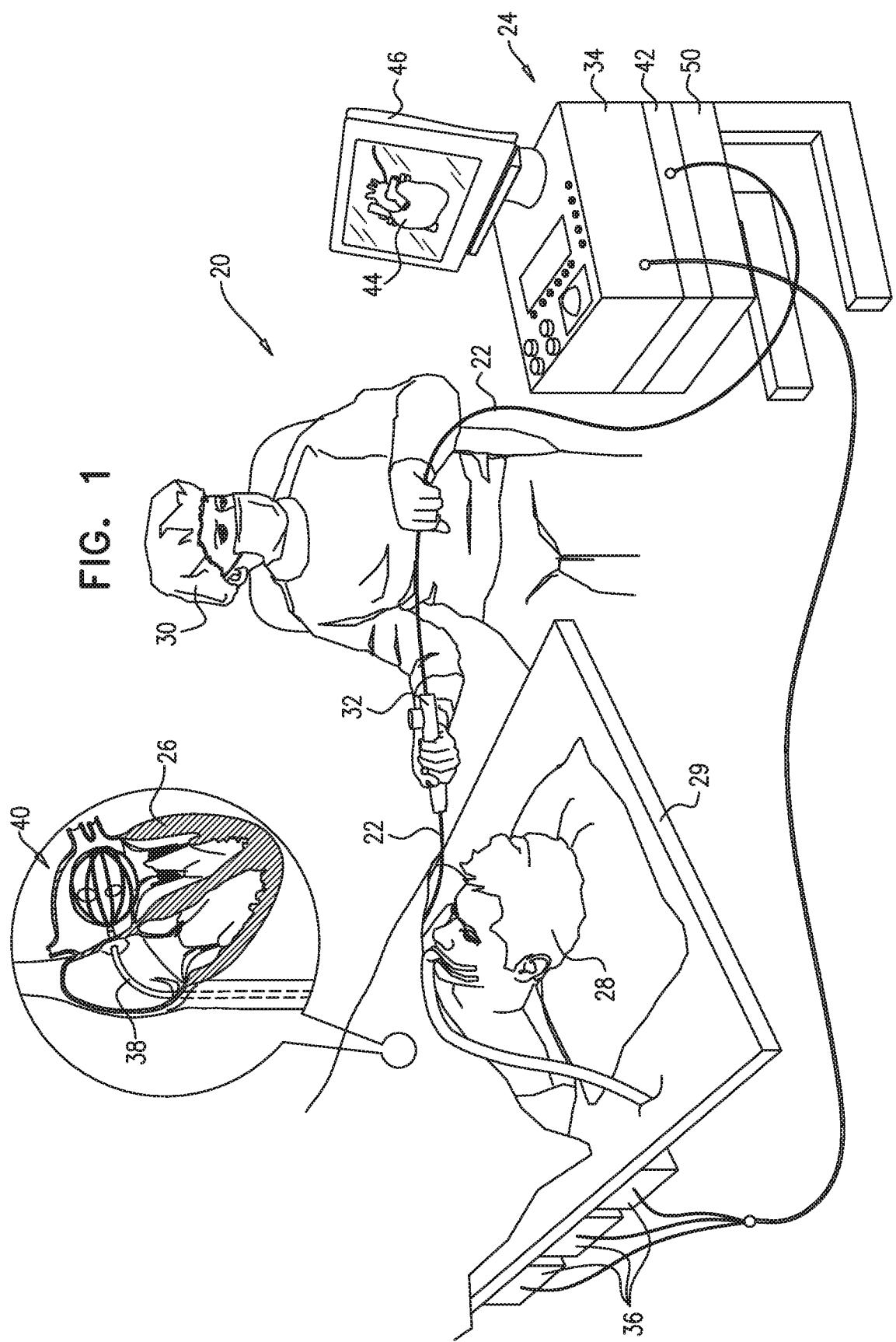
FIG. 1 is schematic pictorial illustration of a system for cardiac catheterization, in accordance with an embodiment of the invention.

Multi-spline catheters, such as basket catheters and multi-arm catheters, are useful in both diagnostic and therapeutic applications. For precise mapping and treatment, it is important that the splines be accurately tracked and positioned within the heart. For this purpose, discrete magnetic sensors may be fixed to the splines. Such sensors typically comprise wire-wound coils, although solid-state devices, such as Hall Effect sensors, are sometimes used. The electrical signals output by the sensors in response to magnetic fields generated in the body can give accurate indications of the locations and orientations of the splines. To accurately track all the splines, however, a large number of sensors is needed, which can make such catheters prohibitively difficult and expensive to manufacture.

Multi-spline catheters can efficiently be made from ribbons of flexible printed circuit board material. In this sort of implementation, the circuit board typically comprises electrodes, which are disposed on the outer surface of each spline so as contact tissue at respective locations within the body. If the locations and orientations of the splines are accurately known, the outputs of the electrodes can be used in mapping electrical activity in the body (particularly within chambers of the heart). Additionally or alternatively, the electrodes may be driven with electrical current in order to ablate the tissue.

Embodiments of the present invention that are described herein provide invasive medical probes having multiple distal splines that are made from ribbons of flexible printed circuit board, and take advantage of this structure in order sense spline positions magnetically, while avoiding the need for discrete field sensors. In the disclosed embodiments, an invasive probe, such as a catheter, comprises an insertion tube, whose distal end is inserted into the body, with flexible splines of this sort deployed from the distal end (for example, in a basket or multi-arm configuration). A conductive trace is formed in at least one layer of the circuit board so as to define one or more coils that are disposed along the length of each spline. One or more magnetic field generators generate magnetic fields within the body of a patient into which the probe is inserted. The electrical signals that are output by the coils in response to these magnetic fields can then be processed in order to derive respective positions of the flexible splines in the body. Since the coils are integrated into the printed circuit ribbons, they are robust and add only negligible manufacturing cost to the probe.

For the sake of clarity and concreteness of illustration, the embodiments described below relate specifically to a basket catheter for deployment inside the heart. The principles of the present invention, however, are not limited to this specific sort of catheter, but may rather be applied to other types of multi-spline catheters, such as multi-arm catheters, as well as to multi-spline probes for use in other body cavities and organs.

FIG. 1 is a schematic, pictorial illustration of a system 20 for cardiac catheterization, in accordance with an embodiment of the present invention. System 20 comprises a catheter 22, which is connected at its proximal end to a control console 24. In the embodiment described herein, catheter 22 may be used for any suitable therapeutic and/or diagnostic purposes, such as ablation of tissue in a heart 26 of a patient 28 and/or mapping of electrophysiological signals for the diagnosis of cardiac pathologies, such as cardiac arrhythmias, for example.

An operator 30 (such as an interventional cardiologist) inserts catheter 22 through the vascular system of patient 28, who is shown lying on a table 29. Catheter 22 comprises an insertion tube 38 with a basket assembly 40 deployed from its distal end, as shown in the figures that follow. Operator 30 advances insertion tube through the vascular system of patient 28 until assembly 40 is located in a desired chamber of heart 26, typically by manipulating a handle 32 connected to the proximal end of the insertion tube. The proximal end of catheter 22 is connected by a cable to interface circuitry 42 in console 24.

Console 24 tracks the locations and orientations of the splines of basket assembly 40 within heart 26 by magnetic position sensing. For this purpose, console 24 comprises a driver circuit 34, which drives magnetic field generators 36 that are placed at known positions external to the body of patient 28, in this case on or below table 29. Basket assembly 40 comprises multiple coils, which are disposed along the lengths of the splines of the basket assembly (as shown in the figures that follow) and output electrical signals in response to the magnetic fields.

Interface circuitry 42 amplifies and digitizes these electrical signals and passes the digital signal values to a processor 50 in console 24. Typically, processor 50 comprises a general-purpose microprocessor, which is programmed in software to process the signals output by the coils in order to derive respective positions of the flexible splines in the body. Additionally or alternatively, at least some of the functions of processor 50 may be implemented in hard-wired or programmable logic. Processor 50 converts the electrical signals to location and orientation coordinates using methods that are implemented, for example, in the CARTO™ system, produced by Biosense Webster, Inc. Such methods are described in detail, for example, in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455, issued as U.S. Pat. No. 6,690,963 on Feb. 10, 2004, 2003/0120150, issued as U.S. Pat. No. 7,729,742 on Jun. 1, 2010 and 2004/0068178, now abandoned, whose disclosures are all incorporated herein by reference. In some embodiments, processor 50 overlays the positions of the splines in basket assembly 40 on a map 44 or other image of heart 26, which is presented on a display screen 46.

Figure 2:
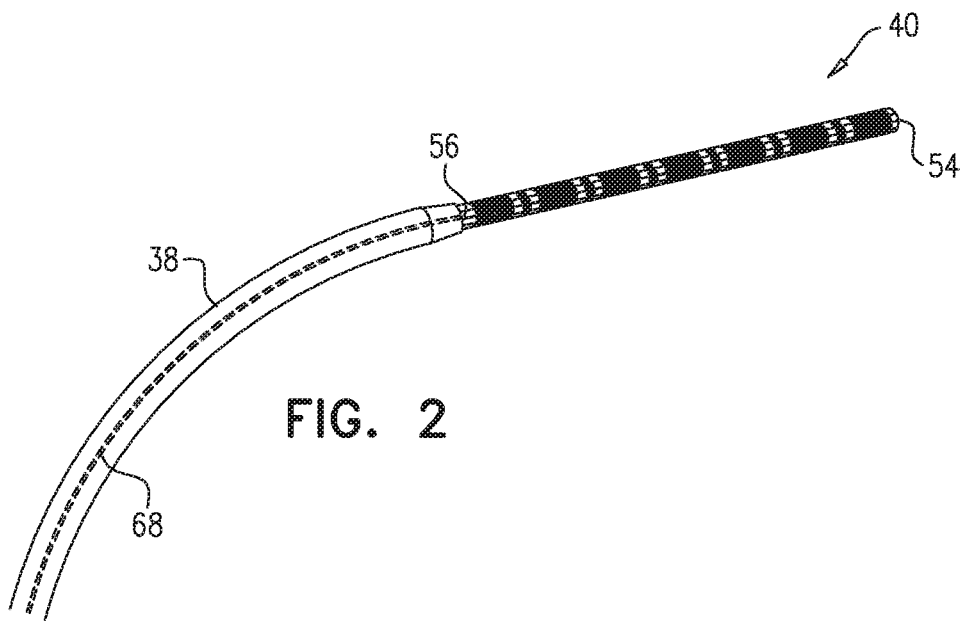
FIGS. 2 and 3 are schematic pictorial illustrations of a basket assembly at the distal end of a catheter in collapsed and expanded configurations, respectively, in accordance with an embodiment of the invention.
Figure 3:
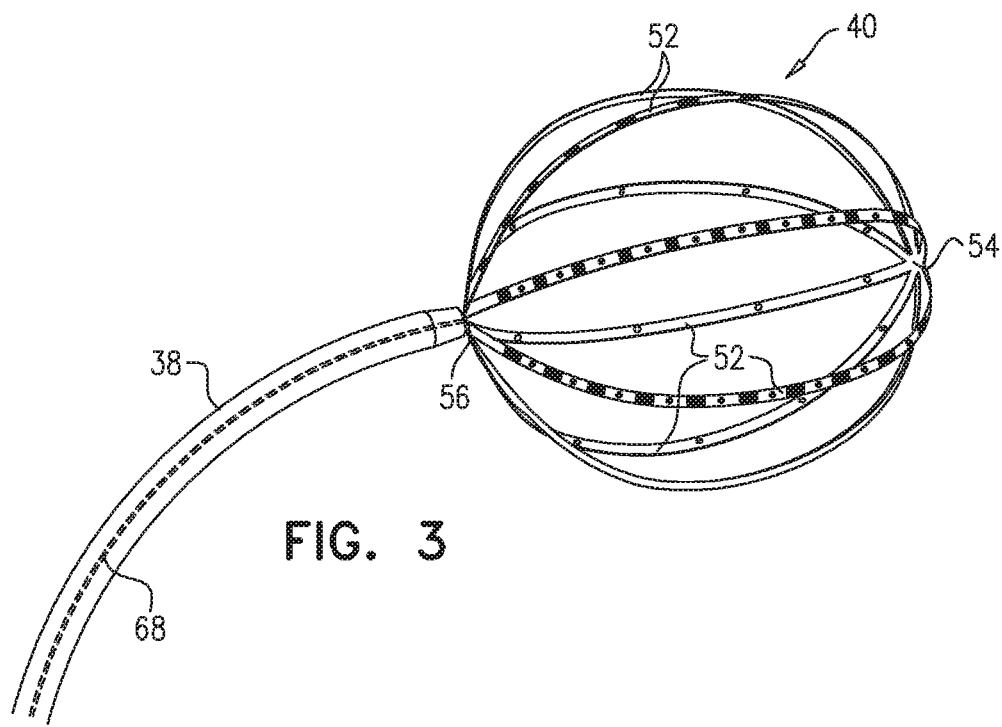

FIGS. 2 and 3 are schematic pictorial illustrations of basket assembly 40 at the distal end of insertion tube 38, in collapsed and expanded configurations, respectively, in accordance with an embodiment of the invention. Assembly 40 comprises multiple splines 52, which are shown in greater detail in FIGS. 4A/B. Splines are connected together at both their distal extremities 54 and proximal extremities 56 to define basket assembly 40. In the collapsed configuration, shown in FIG. 2, splines 52 are held parallel to insertion tube 38 during insertion into the body. In the expanded configuration, shown in FIG. 3, splines 52 bow radially outward within a cavity in the body, such as in the left atrium of heart 26 as shown in FIGS. 1 and 5. Operator 30 is able to change the configuration of basket assembly 40 as desired, for example using suitable controls on handle 32.

Figure 4A:
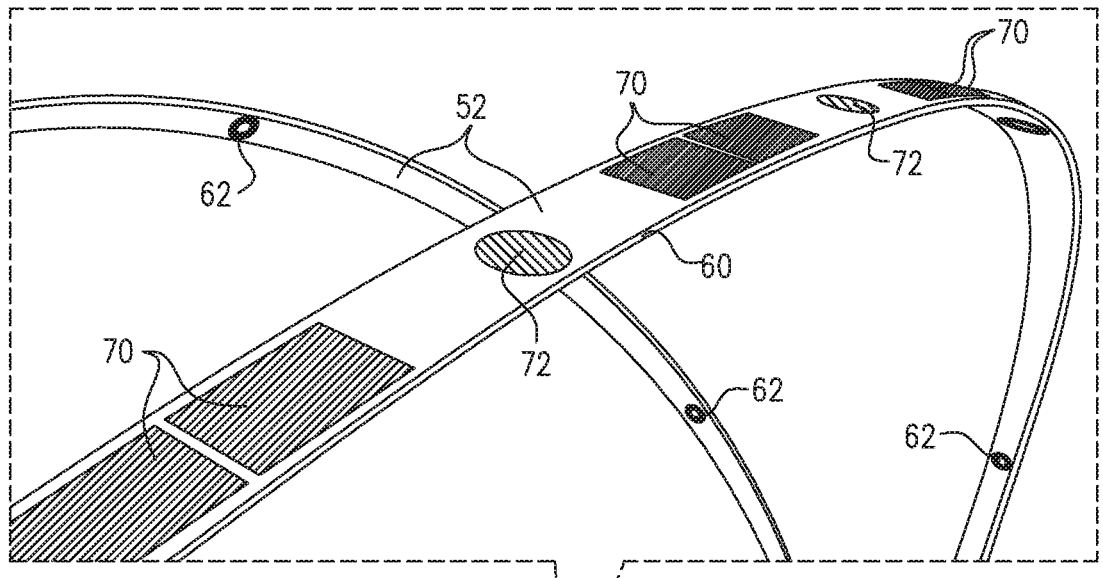
FIGS. 4A and 4B are schematic, detail views of structures on the splines of the basket assembly shown in FIG. 3, in accordance with an embodiment of the invention.
Figure 4B:
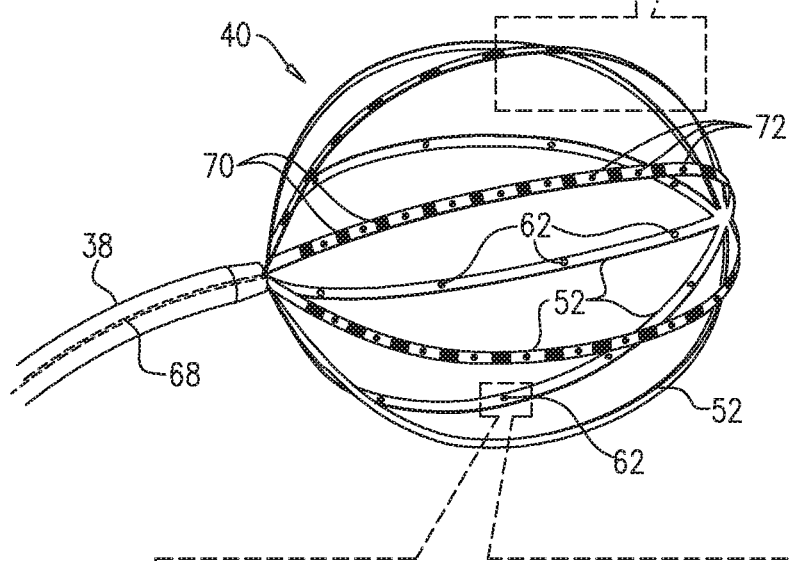
Figure 4B:
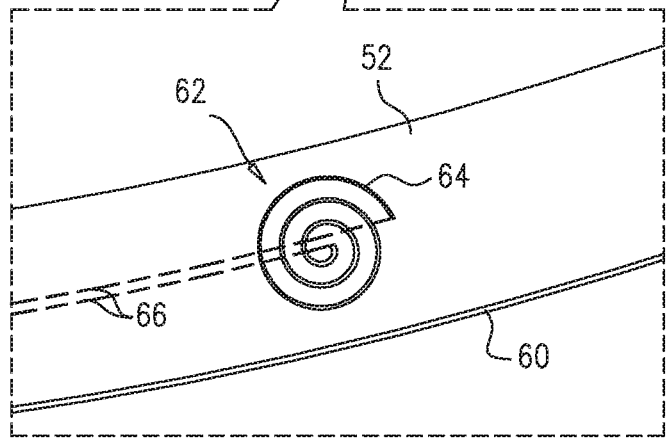
Figure 5:
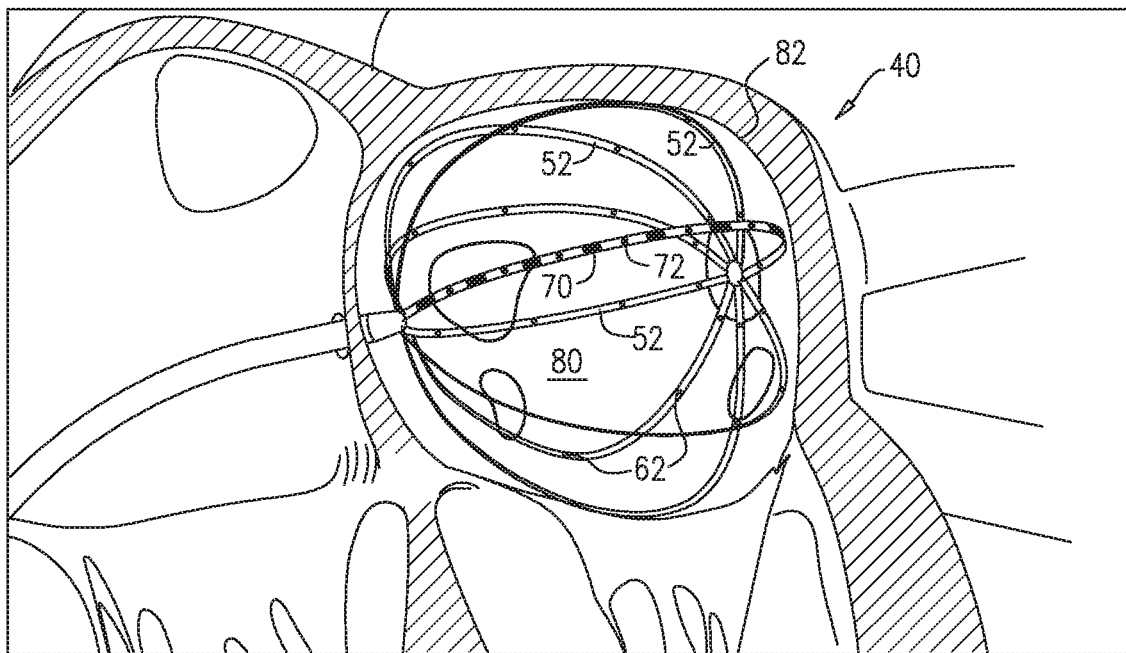
FIG. 5 is a schematic pictorial illustration of the basket assembly of FIGS. 2 and 3 when deployed in a chamber of a heart, in accordance with an embodiment of the invention.

FIGS. 4A and 4B are schematic, detail views of structures on splines 52 of basket assembly 40, in accordance with an embodiment of the invention. Each spline 52 comprises a ribbon of flexible, multilayer circuit board 60, thus forming an arm that is flexible about its longitudinal axis. Flexible circuit board 60 typically comprises a suitable polymer substrate, such as polyimide (which is sold under the trade name Kapton™), or from any other suitable material that allows for bending between the collapsed and expanded configurations. Typically, the circuit structures on board 60 include multiple, successive layers of metal traces and dielectric material deposited on the substrate, with vias interconnecting the metal traces in different layers, as is known in the art. For ease of manufacturing, the structures on multiple ribbons may be fabricated side-by-side on a single substrate and then sliced apart (using laser cutting, for example) to separate the ribbons.

In some embodiments, circuit board 60 has a resilience sufficient to cause splines 52 to bow radially outward when released (within a cavity such as a heart chamber, for example). In this case, there is no need for any additional strengthening member, such as a metal or plastic filament, along the splines. Alternatively, a strengthening element may be coupled along circuit board 60 in order to mechanically strengthen the spline.

Circuit board 60 comprises coils 62, which are disposed along the length of each spline 52 and output electrical signals in response to the magnetic fields applied by field generators 36. Each coil 62 comprises a conductive trace 64 that is formed in at least one layer of circuit board 60. Multi-level coils, with increased inductance, may be formed by interconnecting loops of traces 64 in different layers of circuit board 60 by via s running between the layers. Further conductive traces 66 are connected to conductive trace 64 of coil 62 and run along the lengths of splines 52 to connect with conductors 68 running through insertion tube and thus couple the electrical signals from the coils via interface circuitry 42 to processor 50 in console 24. Processor 50 digitally processes these signals, explained above, in order to derive respective location and orientation coordinates of coils 62, and thus find the positions of the splines 52 in which the coils are embedded.

In the pictured embodiment, circuit board 60 also comprises embedded electrodes 70, which are disposed on the outer surface of splines 52 so as contact tissue at respective locations within the body when basket assembly 40 is expanded. Electrodes 70 thus output signals in response to electrical activity in the tissue, and these signals are conveyed via additional conductive traces (not shown) on or in circuit board 60 and conductors 68 to processor 50. The processor is then able to map electrical activity in the body based on the electrical activity sensed by electrodes 70 and the positions of the flexible splines 52 that are derived from the signals output by coils 62. Additionally or alternatively, console 24 may drive electrodes 70 with high-power radio-frequency (RF) currents in order to ablate tissue in heart 26 with which the electrodes are in contact.

As another option, additionally or alternatively, acoustic transducers 72, such as miniature piezoelectric crystals, can be fixed to circuit board 60 on one or more of splines 52. Circuit board 60 comprises further conductive traces (not shown), which are connected to acoustic transducers 72 and run along the length of splines 52 and connect to conductors 68 so as to couple the transducers to console 24. Typically, console 24 drives transducers 72 to transmit and receive ultrasound beams in A-mode. In this mode, processor 50 measures the time of flight of the ultrasound waves that are reflected from the heart wall back to each transducer 72. This measurement can give an indication of the electrode-tissue distance and/or the thickness of the heart wall at the location of the transducer.

FIG. 5 is a schematic pictorial illustration of the basket assembly of FIGS. 2 and 3 when deployed in the expanded configuration in a left atrium 80 of heart 26, in accordance with an embodiment of the invention. Splines 52 bow resiliently outward, while operator 30 (FIG. 1) exerts forward pressure so that the splines engage an inner wall 82 of atrium 80 along substantial portions of their lengths. Coils 62 output signals that enable processor 50 to derive the positions of splines 52 and possibly to display these positions on screen 46.

The signals output by acoustic transducers 72 give an indication as to the locations where splines 52 are in close contact with wall 82. Alternatively or additionally, processor 50 may evaluate the quality of contact by measuring the impedance between each of electrodes 70 and the tissue of wall 82, as is known in the art. Further additionally or alternatively, based on the electrical activity sensed by electrodes 70 that are in contact with the tissue of wall 82 and the coordinates of coils 62, processor 50 constructs map 44 showing topographical features of atrium 80 and the distribution of electrical activity relative to these topographical features.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A medical apparatus, comprising:
   one or more magnetic field generators, which are configured to generate magnetic fields within a body of a patient; and an invasive probe, which includes:
  an insertion tube defining a longitudinal axis and having a distal end, which is configured for insertion into the body,
  a plurality of flexible splines configured to be deployed from the distal end of the insertion tube, each of the flexible splines including a flexible, multilayer circuit board defining an inward facing surface and an outward facing surface on an exterior of each of the flexible splines relative to the longitudinal axis, and including a conductive trace that is formed in at least one layer of the flexible, multilayer circuit board, the conductive trace being configured to define one or more coils, which are disposed along a length of the inward facing surface of each of the flexible splines, each of the one or more coils being operable to output electrical signals in response to the magnetic fields, each of the one or more coils being positioned on the inward facing surface of each of the flexible splines such as to not contact a tissue of the body when the outward facing surface of each of the flexible splines is in contact with the tissue, and
  a processor, which is coupled to receive and process the electrical signals output by the one or more coils in order to derive respective positions of the flexible splines in the body.

2. The medical apparatus according to claim 1, the flexible splines having respective distal and proximal extremities and being connected together at both the distal and proximal extremities to define a basket assembly, which has a collapsed configuration, in which the flexible splines are held parallel to the insertion tube during insertion into the body, and an expanded configuration, in which the flexible splines bow radially outward within a cavity in the body.

3. The medical apparatus according to claim 2, the flexible, multilayer circuit board having a resilience sufficient to cause the flexible splines to bow radially outward within the cavity.

4. The medical apparatus according to claim 1, the flexible, multilayer circuit board including further conductive traces, which are connected to the one or more coils and run along the length of the flexible splines so as to couple the electrical signals to the processor.

5. The medical apparatus according to claim 1, the flexible, multilayer circuit board including electrodes, which are disposed on the outward facing surface of each of the flexible splines so as to contact the tissue at respective locations within the body.

6. The medical apparatus according to claim 5, the processor being configured to map electrical activity in the body responsively to the electrical activity sensed by the electrodes and the positions of the flexible splines that are derived from the signals output by the one or more coils.

7. The medical apparatus according to claim 1, the one or more coils including multiple coils disposed along the length of each of the flexible splines, and the processor being configured to derive both locations and orientations of the flexible splines from the electrical signals output by the multiple coils.

8. A method for medical diagnosis or treatment, the method comprising:
  generating magnetic fields within a body of a patient;
  inserting a distal end of an insertion tube into the body, the insertion tube defining a longitudinal axis;
  deploying a plurality of flexible splines from the distal end of the insertion tube into the body, each of the flexible splines comprising a flexible, multilayer circuit board and a conductive trace that is formed in at least one layer of the flexible, multilayer circuit board, the conductive trace being configured to define one or more coils, which are disposed along a length of each of the flexible splines at inward facing exterior positions of each of the flexible splines relative to the longitudinal axis such as to not contact tissue of the body when an outward facing exterior position of each of the flexible splines relative to the longitudinal axis is in contact with the tissue, each of the one or more coils being operable to output electrical signals in response to the magnetic fields; and
  processing the electrical signals output by the one or more coils in order to derive respective positions of each of the flexible splines in the body.

9. The method according to claim 8, the flexible splines having respective distal and proximal extremities and are connected together at both the distal and proximal extremities to define a basket assembly, which has a collapsed configuration, in which the flexible splines are held parallel to the insertion tube during insertion into the body, and deploying the flexible splines includes expanding the basket assembly so that the flexible splines bow radially outward within a cavity in the body.

10. The method according to claim 9, the flexible, multilayer circuit board having a resilience sufficient to cause the flexible splines to bow radially outward within the cavity.

11. The method according to claim 8, the flexible, multilayer circuit board including further conductive traces, which are connected to the one or more coils and run along the length of the flexible splines so as to couple the electrical signals to a processor.

12. The method according to claim 8, the flexible, multilayer circuit board including electrodes, which are disposed on an outer surface of each of the flexible splines so as to contact the tissue at respective locations within the body.

13. The method according to claim 12, and including mapping electrical activity in the body responsively to the electrical activity sensed by the electrodes and the positions of the flexible splines that are derived from the signals output by the one or more coils.

14. The method according to claim 8, the one or more coils including multiple coils disposed along the length of each of the flexible splines, and wherein the method includes deriving both locations and orientations of the flexible splines from the electrical signals output by the multiple coils.

15. A medical apparatus, comprising:
  one or more magnetic field generators, which are configured to generate magnetic fields within a body of a patient; and
  an invasive probe defining a longitudinal axis and having a distal end, which is configured for insertion into the body, including:
    a plurality of flexible splines configured to be deployed from the distal end of the invasive probe, each of the flexible splines including a flexible circuit board defining an inward facing surface and an outward facing surface on an exterior of each of the flexible splines relative to the longitudinal axis,
    a plurality of coils disposed along the inward facing surface of each of the flexible splines such as to not contact a tissue of the body within a cavity when the outward facing surface of each of the flexible splines are in contact with the tissue, each of the plurality of coils being operable to output electrical signals in response to the magnetic fields, and a plurality of electrodes disposed along the outward facing surface of each of the flexible splines so as to contact the tissue.

16. The medical apparatus according to claim 15, the flexible splines having respective distal and proximal extremities and being connected together at both the distal and proximal extremities to define a basket assembly, which has a collapsed configuration, in which the flexible splines are held parallel to the invasive probe during insertion into the body, and an expanded configuration, in which the flexible splines bow radially outward within the cavity.

17. The medical apparatus according to claim 15, the flexible circuit board having a resilience sufficient to cause the flexible splines to bow radially outward within the cavity.

18. The medical apparatus according to claim 15, further comprising:

a processor configured to receive and process the electrical signals output by the plurality of coils in order to derive respective positions of the flexible splines within the cavity.

19. The medical apparatus according to claim 18, the flexible circuit board including conductive traces coupled with the plurality of coils so as to couple the electrical signals with the processor.

20. The medical apparatus according to claim 18, the plurality of coils being disposed along a length of each of the flexible splines, and the processor being configured to derive both locations and orientations of the flexible splines from the electrical signals output by the multiple coils.

* * * * *